(12) United States Patent
Liu

(10) Patent No.: US 6,517,814 B2
(45) Date of Patent: Feb. 11, 2003

(54) MACROCYCLIC CHELANTS USEFUL FOR METALLOPHARMACEUTICALS

(75) Inventor: Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/033,765

(22) Filed: Dec. 27, 2001

(65) Prior Publication Data

US 2002/0098149 A1 Jul. 25, 2002

Related U.S. Application Data

(60) Provisional application No. 60/260,500, filed on Jan. 9, 2001.

(51) Int. Cl.$^7$ .............................................. A61B 5/055
(52) U.S. Cl. .................... 424/9.36; 424/1.11; 424/1.65; 424/9.1; 424/9.3; 424/9.362; 424/9.4; 424/9.361; 534/10; 534/14
(58) Field of Search .............................. 424/1.11, 1.65, 424/9.1, 9.3, 9.4, 9.42, 9.361, 9.362, 9.5, 9.6, 9.7, 9.8; 534/7, 10–16

(56) References Cited

U.S. PATENT DOCUMENTS

| | | |
|---|---|---|
| 4,678,667 A | 7/1987 | Meares et al. |
| 4,885,363 A | 12/1989 | Tweedle et al. |
| 4,923,985 A | 5/1990 | Gansow et al. |
| 5,053,053 A | 10/1991 | De Labbey et al. |
| 5,206,370 A | 4/1993 | Schwartz et al. |
| 5,310,535 A | 5/1994 | Kruper, Jr. et al. |
| 5,428,154 A | 6/1995 | Gansow et al. |
| 5,428,156 A | 6/1995 | Mease et al. |
| 5,474,756 A | 12/1995 | Tweedle et al. |
| 5,739,323 A | 4/1998 | Kruper, Jr. et al. |
| 5,744,120 A | 4/1998 | Edwards et al. |
| 5,756,065 A | 5/1998 | Wilson et al. |
| 5,846,519 A | 12/1998 | Tweedle et al. |
| 5,958,374 A | 9/1999 | Meares et al. |
| 6,107,482 A | 8/2000 | Cook et al. |

FOREIGN PATENT DOCUMENTS

| | | |
|---|---|---|
| EP | 292689 B1 | 11/1988 |
| EP | 382583 B1 | 8/1990 |
| EP | 441953 B1 | 8/1991 |
| EP | 565930 B1 | 10/1993 |
| EP | 569132 B1 | 10/1993 |
| WO | WO 87/05030 | 8/1987 |
| WO | WO 89/01476 | 2/1989 |
| WO | WO 89/11475 | 11/1989 |
| WO | WO 90/12050 | 10/1990 |
| WO | WO 91/14458 | 10/1991 |
| WO | WO 93/06868 | 4/1993 |
| WO | WO 95/26202 | 10/1995 |
| WO | WO 96/30377 | 10/1996 |
| WO | WO 97/32862 | 9/1997 |

OTHER PUBLICATIONS

Song et al, May/Jun. 2001, Can. J. Chem., vol. 79, pp. 1058–1067.*
*Nature* 1974 250, 587.
Krejcarek and Tucker (*Biochem. Biophys. Res. Commun.* 1976, 77, 581.
Hnatowich et al, *Science* 1983, 220, 613.
*Inorg. Chem.* 1986, 25, 2772.
*Anal. Biochem.* 1985, 148, 249.
*Nucl. Med. Biol.* 1986, 13, 363.
*Inorg. Chem.* 1987, 26, 3458.
Dewanjee, M. K. *Semin. Nucl. Med.* 1990, 20, 5.
Liu, et al *Pure & Appl. Chem.* 1991, 63, 427.
Gansow et al (*Bioconjugate Chem.* 1991, 2, 187.
Liu, et al *Pure & Appl. Chem.* 1991, 63, 427.
Griffiths et al., *Bioconj. Chem.* 1992, 3, 91.
Jurisson, et al *Chem. Rev.* 1993, 93, 1137.
Liu, et al *Bioconj. Chem.* 1997, 8, 621.
Hom et al., *Nucl. Med. Biol.* 1997, 24, 485.
Dilworth, J. R. and Parrott, S. J. *Chem. Soc. Rev.* 1998, 27, 43.
P. Kong Thoo Lin et al., Synthesis, Jun. 1998, 859–866.
Kuksa et al, Synthesis 1999, 6, 1034–1038.

* cited by examiner

Primary Examiner—Dameron L. Jones
(74) Attorney, Agent, or Firm—Woodcock Washburn LLP

(57) ABSTRACT

Macrocyclic chelant are disclosed, as well as chelates of the chelants with metal ions to form radiopharmaceutical and radioactive, MRI and X-ray or CT imaging compounds and compositions. Therapeutic and imaging methods of use are also disclosed.

43 Claims, No Drawings

MACROCYCLIC CHELANTS USEFUL FOR METALLOPHARMACEUTICALS

This application claims the benefit of U.S. Provisional Application No. 60/260,500, filed Jan. 9, 2001, the disclosure of which is incorportated herein by reference in its entirety.

FIELD OF THE INVENTION

This invention relates to new macrocyclic chelants and metal chelates thereof, methods of preparing the chelants and metal chelates, and pharmaceutical compositions comprising the macrocyclic chelants and metal chelates. This invention relates particularly to the use of the new metal chelates as contrast agents in X-ray or CT, MRI imaging, and radiopharmaceuticals for the diagnosis of cardiovascular disorders, infectious disease and cancer. This invention also relates to new bifunctional chelants (BFCs) for attaching diagnostic and therapeutic isotopes to target-specific biomolecules such as proteins, peptides, peptidomimetics, and non-peptide receptor ligands. In addition, the macrocyclic chelants are useful for heavy metal detoxification.

BACKGROUND OF THE INVENTION

Medical imaging modalities, such as MRI, X-ray, gamma scintigraphy, and CT scanning, have become extremely important tools in the diagnosis and treatment of various diseases and illness. The imaging of internal body parts relies on the contrast between the targeted organ and the surrounding tissues. The targeted organs or tissues are visible by the use of a particular metallopharmaceutical contast agent. In X-ray and CT diagnostics, increased contrast of internal organs, such as the kidney, the urinary tract, the digestive tract, the cardiovascular system, tumors, and so forth is obtained by administering a contrast agent which is substantially radiopaque. In conventional proton MRI diagnostics, increased contrast of internal organs and tissues may be obtained by administrating compositions containing paramagnetic metal species, which increase the relativity of surrounding water protons. In ultrasound diagnostics, improved contrast is obtained by administering compositions having acoustic inpedances different from that of blood and other tissues. In gamma scintigraphy, contrast of internal organ is obtained by the specific localization of a gamma ray emitting radiopharmaceutical.

Attachment of metal ions to biomolecules (BM) such as antibodies, antibody fragments, peptides, peptidomimetics, and non-peptide receptor ligands leads to useful target-specific diagnostic and therapeutic metallopharmaceuticals. These include fluorescent, radioactive and paramagnetic metal ions attached to proteins that can be used as probes in vivo in biological systems and in vitro in analytical systems as radioimmunoassays. For example, attachment of radionuclides to monoclonal antibodies that recognize tumor associated antigens provides radioimmunoconjugates useful for cancer diagnosis and therapy. The monoclonal antibodies are used as carriers of desired radioisotope to the tumor in vivo.

Radiopharmaceuticals can be classified into two primary classes: those whose biodistribution is determined exclusively by their chemical and physical properties; and those whose ultimate distribution is determined by receptor binding or other biological interactions. The latter class is often called target-specific radiopharmaceuticals. In general, a target specific radiopharmaceutical can be divided into four parts: a targeting molecule, a linker, a BFC, and a radionuclide.

The targeting molecule serves as a vehicle, which carries the radionuclide to the receptor site at the diseased tissue or organ. The targeting molecules can be macromolecules such as antibodies; they can also be small biomolecules: peptides, peptidomimetics, and non-peptide receptor ligands. The choice of biomolecule depends upon the targeted disease or disease state.

The radionuclide is the radiation source. The selection of radionuclide depends on the intended medical use (diagnostic or therapeutic) of the radiopharmaceutical. Radionuclides, such as $^{99m}$Tc, $^{131}$I, $^{123}$I, $^{117m}$SN, $^{111}$IN, $^{97}$Ru, $^{203}$Pb, $^{67}$Ga, $^{68}$Ga, $^{89}$Zr, and $^{64}$Cu, are γ-emitters useful for diagnostic imaging. Nearly 80% of radiopharmaceuticals used in nuclear medicine are $^{99m}$Tc-labeled compounds. The reason for such a preeminent position of $^{99m}$Tc in clinical use is its extremely favorable physical and nuclear characteristics. The 6 h half-life is long enough to allow a radiochemist to carry out radiopharmaceutical synthesis and for nuclear medicine practitioners to collect useful images. At the same time, it is short enough to permit the administration of millicurie amounts of $^{99m}$Tc radioactivity without significant radiation dose to the patient. The monochromatic 140 KeV photons are readily collimated to give images of superior spatial resolution. $^{99m}$Tc is readily available from commercial $^{99}$Mo-$^{99m}$Tc generators at low cost. Radionuclides, such as $^{90}$Y, $^{177}$Lu, $^{149}$Pm, $^{153}$Sm, $^{166}$Ho, $^{131}$I, $^{32}$p, $^{211}$At, $^{47}$SC, $^{109}$Pd, $^{105}$Rh, $^{186/188}$Re, and $^{67}$CU, are potentially useful for radiotherapy. Among these therapeutic radionuclides, lanthanide radioisotopes are of particular interest. There are several lanthanide isotopes to choose, including low energy β-emitter $^{177}$Lu, medium energy β-emitters, $^{149}$Pm and $^{153}$Sm, and high-energy β-emitters, $^{166}$Ho and $^{90}$Y. Yttrium and lanthanide metals share similar coordination chemistry. The chelator technology and their coordination chemistry are well developed and well understood.

Between the targeting molecule and the radionuclide is the BFC, which binds strongly to the metal ion and is covalently attached to the targeting molecule either directly or through a linker. Selection of a BFC is largely determined by the nature and oxidation state of the metallic radionuclide. The linker can be a simple hydrocarbon chain or a long poly(ethylene glycol) (PEG), which is often used for modification of pharmacokinetics. Sometimes, an anionic poly (amino acid) is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelants. The coordination chemistry of the metallic radionuclide will determine the geometry and solution stability of the metal chelate. Different metallic radionuclides have different coodination chemistries, and require BFCs with different donor atoms and ligand frameworks. For "metal essential" radiopharmaceuticals, the biodistribution is exclusively determined by the chemical and physical properties of the metal chelate. For target-specific radiopharmaceuticals, however, the "metal label" is not totally innocent because the target uptake and biodistribution will be affected by not only the targeting biomolecule but also the metal chelate and the linker. This is especially true for radiopharmaceuticals based on small molecules such as peptides due to the fact that in many cases the metal chelate contributes greatly to the overall size and molecular weight. Therefore, the design and selection of the BFC is very important for the development of a new radiopharmaceutical.

The same principle used for target-specific metalloradiopharmaceuticals also applies to target-specific MRI contrast and ultrasound agents. Unlike the target-specific metalloradiopharmaceutical, where the excess unlabeled biomolecule can compete with the radiolabeled BFC-BM conjugate and block the docking of the radiolabeled receptor ligand, MRI and ultrasound contrast agents contain no excess unlabeled BFC-BM conjugate. Saturation of the receptor sites will maximize the contrast between the diseased tissues and normal tissue provided that the use of a relatively large amount of metal-BFC-BM chelate does not cause unwanted side effects.

For a therapeutic radiopharmaceutical or an MRI contrast agent, it is especially important to keep the metal chelate intact under physiological conditions, particularly in the presence of native chelators, such as transferrin, which have very high affinity for trivalent lanthanide metal ions. This requires the chelant to form a metal chelate with high thermodynamic stability and kinetic inertness.

Several BFC systems such as ethylenediaminetetraacetic acid (EDTA) and diethylenetriaminepetaacetic acid (DTPA), as well as their derivatives, have been reported to form thermodynamically stable metal chelates. EDTA-based BFCs were first developed by Sunberg et al (*Nature* 1974, 250, 587) in the 1970s. Krejcarek and Tucker (*Biochem. Biophys. Res. Commun.* 1976, 77, 581) developed an activated DTPA analog via a mixed anhydride, which can be linked to proteins. Later, Hnatowich et al (*Science* 1983, 220, 613) used the cyclic anhydride of DTPA for the same purpose. These linear BFCs bond to a variety of metal ions like $^{111}$In or $^{90}$Y and form thermodynamically stable metal chelates. However, metal chelates of linear BFCs are kinetically labile, which contributes to the loss of radionuclide from the metal chelate and often leads to severe bone marrow toxicity. Gansow et al (*Bioconjugate Chem.* 1991, 2, 187; *Inorg. Chem.* 1986, 25, 2772) prepared a series of substituted DTPA analogs, which form metal chelates with improved solution stability.

Polyaza macrocycles have been widely used as chelants for a variety of transition metals. The macrocyclic polyaminocarboxylates such as 1,4,7,10-tetraazacyclo-dodecane-1, 4,7,10-tetracetic acid (DOTA) and 1,4,8,11-tetraazacyclotetradecane-1,4,8,11-tetracetic acid (TETA) are known to form highly stable metal chelates due to their highly preorganized macrocyclic ligand framework. Their Gd chelates have been widely used as MRI contrast agents. Examples include gadolinium complexes Gd-DOTA (Dotarem™, Guerbet/France), Gd-HP-DO3A (ProHance™, Bracco/Italy), and Gd-DO3A-butrol (Gadovist™, Schering/Germany).

Macrocyclic chelants such as DOTA have also been used as BFCs for the radiolabeling of proteins (antibodies or antibody fragments) and peptides with various diagnostic and therapeutic radionuclides (such as $^{111}$In and $^{90}$Y). Meares and coworkers were the first to synthesize macrocyclic BFCs (*Anal. Biochem.* 1985, 148, 249; *Nucl. Med. Biol.* 1986, 13, 363; *Inorg. Chem.* 1987, 26, 3458), which form $^{67}$Cu and $^{90}$Y chelates with high thermodynamic stability and kinetic inertness. Macrocyclic chelants with three-dimensional cavities are of particular interest because of the high stability of the metal chelates, the substantial selectivity for certain metal ions, either by enforcing a specific spatial arrangement of donor atoms or by introducing different donor atoms into the ligand backbone, and their capability to adopt a preorganized conformation in the unchelated form. The higher the degree of preorganization of an unchelated ligand, the more stable the complex is.

Preorganization of a polydentate chelant results in not only the high thermodynamic stability but also the increased kinetic inertness of its metal chelate. This has been exemplified by the fact that the half-life for $[Gd(DOTA)]^-$ in 0.1 M HCl is 60.2 h and 2000 years at pH=6.0 while the complex $[Gd(DTPA)]^{2-}$ having comparable thermodynamic stability decomposes rapidly under acidic conditions with a half-life of ~1.0 min. The highly preorganized macrocyclic framework of DOTA forces four acetate chelating arms to adopt such a conformation that the metal ion can be completely wrapped by an $N_4O_4$ donor set. At the same time, this also makes it more difficult for the coordinated acetate to be dissociated from the metal center. Therefore, preorganization should be an important factor in the design of new BFCs for the radiolabeling of biomolecules.

Generally, there are three possible approaches to attach a biomolecule to a DOTA-based chelant. In the first approach, the attachment is at one of the carbon atoms of the macrocyclic chelator backbone. In principle, this will result in formation of eight possible isomers when coordinated to the lanthanide metal ion. In the second approach, the linker is attached to the methylene-carbon atom of one of four acetate chelating arms, which may also result in formation of eight possible isomeric forms. In both approaches, the conjugation of the biomolecule does not lead to a significant change in the thermodynamic stability and kinetic inertness of the metal chelate as compared to those of the DOTA chelate. In the third approach, the biomolecule is conjugated to one of the four acetate groups via a CO—N amide bond. Compared to the carboxylate-O, the carbonyl-O is a relatively weak donor for yttrium and lanthanide metal ions. This often leads to the lower thermodynamic stability of the corresponding metal chelate. However, the kinetic inertness of its metal complex remains relatively unchanged.

In U.S. Pat. No. 4,678,667, Meares et al disclosed a copper chelate conjugate for diagnostic or therapeutic applications. The bifunctional macrocyclic chelants include substituted DOTA, TETA, TRITA, HETA. The linker is at least 8-atoms in length and the attachment position of the linker is on the carbon atom of the polyamine macrocycle. U.S. Pat. No. 5,428,156 disclosed a method of producing DOTA, TETA, DOTA-NHS(NHS=N-hydroxysuccinimide) and TETA-NHS esters for conjugation of biomolecule. Meares et al (WO 95/26206 and U.S. Pat. No. 5,958,374) also disclosed a method for preparing a radionuclide-labeled chelating agent complex. It specifically disclosed DOTA $(Gly)_3$-L-(p-isothiocyanato)-Phe-amide as the BFC. The pendant linkers also include —$CH_2CO$—$(AA)_m$—(AA-Phe-Gly), where AA represents an amino acid diradical, more preferably the glycine diradical —$NHCH_2CO$—. Gansow et al (WO 89/11475, WO 91/14458 and U.S. Pat. Nos. 4,923,985 and 5,428,154) disclosed a process of making 4-aminophenyl-DOTA and its use as a BFC for the radiolabeling of biomolecules such as antibody.

Parker et al (WO 87/05030, WO89/01476 and EP 382, 583) disclosed a series of DOTA analogs as BFCs, which are coupled with biomolecules such as proteins, especially antibodies, peptides or carbohydrates to form conjugate compounds. The linker and conjugation group is attached to either one of the four acetate chelating arms or one of the carbon atom of the macrocyclic backbone. Watson, et al (WO 90/12050 and WO 93/06868) disclosed polychelants and their metal chelates useful in diagnostic imaging and in radiotherapy. The macrocyclic chelant moieties are linked to the backbone moiety (dendrimer or polylysine) via an amide-bond. In U.S. Pat. No. 5,053,053, Dean et al also disclosed a series of DOTA and DO3A analogs as BFCs. For DO3A-based BFCS, the conjugation group is connected to a linker attached to one of the four amine-nitrogen atoms. For DOTA derivatives, the linker group is connected to either one of carbon-atoms on the macrocyclic backbone or the methylene-carbon atom of one of the four acetate chelating arms. Tweedle, et al (EP 292,689; U.S. Pat. Nos. 4,885,363, 5,474,756, and 5,846,519) disclosed metal chelates, particularly those of neutral charge, for MRI contrast imaging. It also disclosed DO3A analogs as BFCs for the radiolabeling of biomolecules.

Kruper et al. (U.S. Pat. Nos. 5,310,535 and 5,739,323) disclosed the DOTA analogs as BFCs for the radiolabeling of proteins. The linker is connected to the acetate chelating arm and the conjugation group is on a benzene ring. It was shown that the DOTA monoamide has better kinetic inertness because of less bone uptake. Kubomura et al. (AU 93-35,519 and EP 565,930) disclosed the use of DO3A—$CH_2CONHCH_2CH_2NH_2$ as the BFC, and the metal chelates of BFC-BM conjugates as diagnostic or therapeutic pharmaceuticals. Gozzin et al (WO 97/32862) disclosed a new class of polychelants, their chelates with metal ions and their physiologically acceptable salts, which can be used, either as they are or in association or formulation with other components, for diagnostic imaging in general or specific contrast agents for specific tissues, organs or body compartments. It specifically discloses DOTA as the BFC, and a process of making these macrocyclic chelants with DO3A—$CH_2CONHCH_2CH_2CHO$ and poly(amino acids) as key intermediates. Wilson et al (U.S. Pat. No. 5,756,065) also disclosed DOTA analogs as BFCs. The conjugation group is attached to a benzene ring and the linker group is connected to one of the four acetate chelating arms.

SUMMARY OF THE INVENTION

This invention relates to new macrocyclic chelants and metal chelates thereof, methods of preparing the chelants and metal chelates, and pharmaceutical compositions comprising the macrocyclic chelants and metal chelates. This invention relates particularly to the use of the new metal chelates as contrast agents in X-ray or CT, MRI imaging, and radiopharmaceuticals for the diagnosis of cardiovascular disorders, infectious disease and cancer. This invention also relates to new bifunctional chelants (BFCs) for attaching diagnostic and therapeutic isotopes to target-specific biomolecules such as proteins, peptides, peptidomimetics, and non-peptide receptor ligands., In addition, the macrocyclic chelants are useful for heavy metal detoxification.

Macrocyclic chelants have now been discovered that can be prepared by a simple "one-pot" synthesis. Advantageously, the heteroatom in the pyrone/pyridinone ring can be used as donors to form 9 or 10-coordinate lanthanide complexes, and form stable complexes with trivalent metal ions such as $In^{3+}$, $y^{3+}$, $Sm^{3+}$, $Gd^{3+}$, $Dy^{3+}$, $Ho^{3+}$, $Yb^{3+}$, and $Lu^{3+}$. Because of the macrocyclic effect, the metal complexes are kinetically inert with respect to dissociation. This is particularly important for the development of therapeutic radiopharmaceu-ticals and MRI contrast agents.

According to one embodiment of the present invention, a macrocyclic chelant is provided, having the formula:

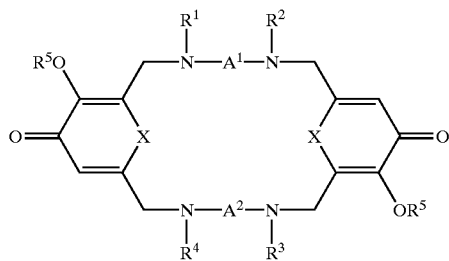

and pharmaceutically acceptable salts thereof, wherein $A^1$ and $A^2$ are independently —$(CH_2)_n$—, wherein n is 2 or 3.

X is selected from: O, NH, or N(OH);

$R^1$, $R^2$, $R^3$, $R^4$, and $R^5$ are independently selected from: H, $C_1$–$C_{10}$ alkyl substituted with 1–5 $R^6$, $C_1$–$C_{10}$ fluoroalkyl sub-stituted with 1–5 $R^6$, $C_2$–$C_{10}$ alkenyl substituted with 1–5 $R^6$, $C_2$–$C_{10}$ fluoroalkenyl substi-tuted with 1–5 $R^6$, aryl substi-tuted with 1–5 $R^6$ and fluoroaryl substituted with 1–5 $R^6$;

$R^6$ is selected from: H, C(=O)$R^7$, C(=O)O$R^8$, C(=O) $NR^7R^8$, PO(O$R^7$)(O$R^8$) and S(O)$_2$O$R^7$;

$R^7$ and $R^8$ are independently selected from: H, $C_1$–$C_{10}$ alkyl substituted with 0–5 $R^9$, $C_3$–$C_{10}$ cycloalkyl substituted with 0–5 $R^9$, $C_1$–$C_{10}$ fluoroalkyl substituted with 0–5 $R^9$, $C_2$–$C_{10}$ alkenyl substituted with 0–5 $R^9$, $C_2$–$C_{10}$ fluoroalkenyl substi-tuted with 0–5 $R^9$, aryl substituted with 0–5 $R^9$ and fluoro-aryl substituted with 0–3 $R^9$, or $R^7$ and $R^8$ may be taken together to form $C_3$–$C_{10}$ cycloalkyl or $C_3$–$C_{10}$ cycloalkenyl optionally interrupted with O, S, NH, S(O), S(O)$_2$, P(O)(O$R^{10}$)O, P(O)(NH$R^{10}$)O, C(O)NH, NHC(O), NHC(O)NH or NHC(S)NH, or NHC(S) NH, or aryl or fluoroaryl substituted with 0–5 $R^{10}$; said $C_1$–$C_{10}$ alkyl or $C_2$–$C_{10}$ alkenyl optionally interrupted with O, S, N$R^{10}$, S(O), S(O)$_2$, P(O)(O$R^{10}$), P(O)(O$R^{10}$)O, P(O)(NH$R^{10}$), P(O)(NH$R^{10}$)O, C(O)NH, NHC(O), NHC(O)NH or NHC(S)NH;

$R^9$ is selected from: H, OH, NH$R^{10}$ C(=O)$R^{10}$ OC(=O) $R^{10}$ OC(=O)O$R^{10}$, C(=O)O$R^{10}$ C(=O)N$R^{10}_2$, PO$_3R^{10}_2$, SR$^{10}$, SOR$^{10}$, SO$_2R^{10}$, NHC(=O)$R^{10}$, NHC(=O)NH$R^{10}$, CH$_2$O$R^{10}$ and NHC(=S)NH$R^{10}$; and $R^{10}$ is selected from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl and fluoro-phenyl.

According to another embodiment of the present invention, a radiopharmaceutical compound is provided, in which the macrocyclic chelant of the present invention is chelated with a radionuclide selected from $^{52m}Mn$, $^{52}F$, $^{55}Co$, $^{60}Cu$, $^{62}Cu$, $^{64}Cu$, $^{67}Cu$, $^{67}Ga$, $^{68}Ga$, $^{90}Y$, $^{94m}Tc$, $^{99m}Tc$, $^{105}Rh$, $^{109}Pd$, $^{111}In$, $^{117m}Sn$, $^{149Pr}$, $^{153}Sm$, $^{159}Gd$, $^{166}Ho$, $^{169}Yb$, $^{177}Lu$, $^{186}Re$, $^{188}Re$, $^{203}Pb$, $^{211}Pb$, and $^{212}Bi$.

According to another embodiment of the present invention, an MRI contrast agent is provided in which the macrocyclic chelant of the present invention is chelated with a paramagnetic metal ion of atomic number 21–29, 42–44 or 58–70.

According to another embodiment of the present invention, an X-ray or CT contrast agent is provided, in which the macrocyclic chelant of the present invention is chelated with a heavy metal ion of atomic number 21–31, 39–49, 50, 56–80, 82, 83 or 90.

According to yet another embodiment of the present invention a conjugate is provided having the formula:

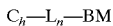

and pharmaceutically acceptable salts thereof, wherein, $C_h$ is the macrocyclic chelant of the present invention wherein one of $R^1$ to $R^{10}$ is a bond to $L_n$;

$L_n$ is a linking group having the formula:

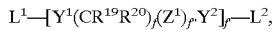

$L^1$ is $-[(CH_2)_g Z^1]_{g'}-(CR^{19}R^{20})_{g''}-$;
$L^2$ is $-(CR^{19}R^{20})_{g''}-[Z^1(CH_2)_g]_{g'}-$;
g is independently 0–10;
g' is independently 0–1;
g" is independently 0–10;
f is independently 0–10;
f' is independently 0–10;
f" is independently 0–1;
$Y_1$ and $Y^2$, at each occurrence, are independently selected from: a bond, O, $NR^{20}$, C=O, C(=O)O, OC(=O)O, C(=O)NH—, C=$NR^{20}$, S, S(O), S(O)$_2$, NHC(=O), (NH)$_2$C(=O) and (NH)$_2$C=S;
$R^{19}$ and $R^{20}$ are independently selected at each occurrence from: H, $C_1$–$C_{10}$ alkyl substituted with 0–5 $R^{21}$ and alkaryl wherein the aryl is substituted with 0–5 $R^{21}$;
$R^{21}$ is independently selected at each occurrence from: $NHR^{22}$, C(=O) $R^{22}$, OC(=O) $R^{22}$, OC(=O) $OR^{22}$, C(=O)$OR^{22}$, C(=O)$NR_2^{22}$, —CN, $SR^{22}$, S(O)$R^{22}$, S(O)$_2R^{22}$, NHC(=O)$R^{22}$, NHC(=O) $NHR^{22}$, NHC(=S) $NHR^{22}$ and a bond to BM;
$R^{22}$ is independently selected at each occurrence from: H, $C_1$–$C_6$ alkyl, benzyl, phenyl and a bond to BM; and
BM is a biologically active molecule selected from: IIb/IIIa receptor ligands, fibrin binding peptides, leukocyte binding peptides, chemotactic peptides, LTB$_4$ receptor antagonists, somatostatin analogs, selectin binding pep-tides, vitronectin receptor antagonists, tyrosine kinase in-hibitors, matrix metalloproteinase inhibitors, oligonucleo-tides, fatty acids, nitroimidazoles, and carbohydrates.

According to another embodiment of the present invention a radiopharmaceutical conjugate is provided, in which the macrocyclic chelant of the conjugate of the present invention is chelated with a radionuclide selected from: $^{52m}$Mn, $^{52}$Fe, $^{55}$Co, $^{60}$Cu, $^{62}$Cu, $^{64}$Cu, $^{67}$Cu, $^{67}$Ga, $^{68}$Ga, $^{90}$Y, $^{94m}$Tc, $^{99m}$Tc, $^{105}$Rh, $^{109}$Pd, $^{111}$In, $^{117m}$Sn, $^{149}$Pr, $^{153}$Sm, $^{159}$Gd, $^{166}$Ho, $^{169}$Yb, $^{177}$Lu, $^{186}$Re, $^{188}$Re, $^{203}$Pb, $^{211}$Pb, and $^{212}$Bi.

According to another embodiment of the present invention, an MRI contrast agent is provided, in which the macrocyclic chelant of the conjugate of the present invention is chelated with a paramagnetic metal ion of atomic number 21–29, 42–44 or 58–70.

According to another embodiment of the present invention, an X-ray or CT contrast agent is provided, in which the macrocyclic chelant of the conjugate of the present invention is chelated with a heavy metal ion of atomic number 21–31, 39–49, 50, 56–80, 82, 83 or 90.

According to another embodiment of the present invention, pharmaceutical compositions are provided for treating pathological processes involving angiogenic neovasculature in a patient in need thereof containing the radiopharmaceutical compounds and conjugates of the present invention and a pharmaceutically acceptable carrier wherein the radionuclide is selected from: $^{64}$Cu, $^{67}$Cu, $^{90}$Y, $^{105}$Rh, $^{109}$Pd, $^{111}$In, $^{117m}$Sn, $^{149}$Pr, $^{153}$Sm, $^{159}$Gd, $^{166}$Ho, $^{169}$Yb, $^{177}$Lu, $^{186}$Re, $^{188}$Re, $^{203}$Pb, $^{211}$Pb, and $^{212}$Bi. When the conjugates of the present invention are employed, BM is preferably selected from: somatostatin analogs, vitronectin receptor antagonists, tyrosine kinase inhibitors, and matrix metalloproteinase inhibitors.

In yet another embodiment of the present invention treatment methods are provided for pathological processes involving angiogenic neovasculature in a patient in need thereof, in which an effective amount of the aforesaid pharmaceutical composition is administered to the patient.

According to another embodiment of the present invention, radioactive imaging compositions are provided containing the radiopharmaceutical compounds and conjugates of the present invention and a pharmaceutically acceptable carrier, wherein the radionuclide is selected from: $^{52m}$Mn, $^{52}$Fe, $^{55}$Co, $^{60}$CU, $^{62}$Cu, $^{64}$Cu, $^{67}$Ga, $^{68}$Ga, $^{94m}$Tc, $^{99m}$Tc, and $^{111}$In.

In yet another embodiment of the present invention, methods for radioactive imaging are provided in which an effective amount of the radioactive imaging compositions of the present invention are administered to a patient to be imaged sufficiently in advance thereto.

According to another embodiment of the present invention, magnetic resonance imaging compositions are provided containing the magnetic resonance imaging compounds and conjugates of the present invention and a pharmaceutically acceptable carrier. In yet another embodiment of the present invention, methods for magnetic resonance imaging are provided in which an effective amount of the magnetic resonance imaging compositions of the present invention are administered to a patient to be imaged sufficiently in advance thereto.

According to another embodiment of the present invention, X-ray and CT imaging compositions are provided containing the X-ray and CT imaging compounds and conjugates of the present invention and a pharmaceutically acceptable carrier. In yet another embodiment of the present invention, methods for X-ray and CT imaging are provided in which an effective amount of the X-ray or CT imaging compositions of the present invention are administered to a patient to be imaged sufficiently in advance thereto.

According to another embodiment of the present invention, compositions for treating heavy metal toxicity in a patient in need thereof are provided containing the polypodal chelant and conjugates thereof of the present invention and a pharmaceutically acceptable carrier. In yet another embodiment of the present invention, methods for treating heavy metal toxicity in a patient in need thereof are provided in which an effective amount of the aforesaid compositions of the present invention are administered to the patient.

Another embodiment of the present invention is diagnostic kits for the preparation of radiopharmaceuticals or radioactive, magnetic resonance, X-ray or CT imaging agents. Diagnostic kits of the present invention comprise one or more vials containing the sterile, non-pyrogenic, formulation comprised of a predetermined amount of a compound of the present; invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The one or more vials that contain all or part of the formulation can independently be in the form of a sterile solution or a lyophilized solid.

DETAILED DESCRIPTION OF THE INVENTION

Macrocyclic chelants according to the present invention have the structure:

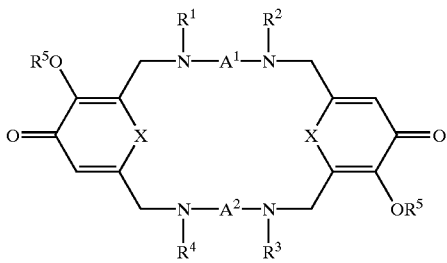

wherein $A^1$, $A^2$, X, $R^1$, $R^2$, $R^3$, $R^4$ and $R^5$ have the above-described values. $A^1$ and $A^2$ are preferably —$(CH_2)_2$—.

$R^1$, $R^2$, $R^3$, $R^4$ and $R^5$ are preferably independently selected from H, $C_1$–$C_3$ alkyl substituted with 1–2 $R^6$, $C_{1-C3}$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$; wherein $R^6$ is preferably independently selected at each occurrence from C(=O)$R^7$, C(=O)O$R^8$, C(=O)N$R^7R^8$, PO(O$R^7$)(O$R^8$) and S(O)$_2$O$R^7$; $R^7$ and $R^8$ are preferably independently selected from H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is preferably selected from OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$.

More preferably, X is O or NH; $R^1$, $R^2$, $R^3$, $R^4$ and $R^5$ are independently selected from H, CH$_2$COOH, CH$_2$C(=O)N$R^7R^8$, CH$_2$PO(O$R^7$)(O$R^8$) and CH$_2$S(O)$_2$OH; and $R^7$ and $R^8$ are independently selected from $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$. Most preferably, $R^1$, $R^2$, $R^3$, $R^4$ and $R^5$ are independently selected from H, CH$_2$COOH, CH$_2$C(=O)NH$_2$, CH$_2$PO(OH)$_2$ and CH$_2$S(O)$_2$OH.

A particularly preferred macrocyclic chelant has the formula:

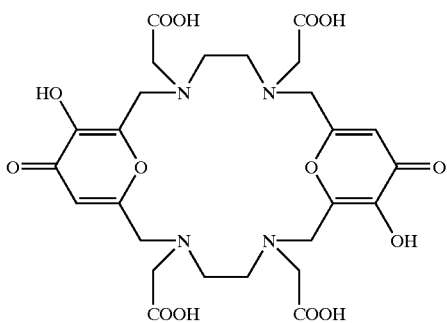

DEFINITIONS

The compounds herein described may have asymmetric centers. Compounds of the present invention containing an asymmetrically substituted atom may be isolated in optically active or racemic forms. It is well known in the art how to prepare optically active forms, such(as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valencylis not exceeded, and that the substitution results in a stable compound. When a substitent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^9$) occurs more than one time in any constituent or formula for a compound, its definition at each occurrence is independent of its definition at every other occurrence. For example, if a group is substituted with 0–2 $R^9$, then said group may optionally be substituted with up to two $R^9$ groups and $R^9$ at each occurrence is selected independently from the definition of $R^9$. Also, combinations of substituents and/or variables are permissi-ble only if such combinations result in stable compounds.

When a bond to a substituent is shown to cross a bond connecting two atoms in a ring, then such substituent may be bonded to any atom on the ring. When a substituent is list-ed without indicating the atom via which such substituent is bonded to the rest of the compound of a given formula, then such substituent may be bonded via any atom in such substituent. Combinations of substituents or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2 v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl. "Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aroma-tic. Examples of such carbocycles include, but are not limi-ted to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclo-octane, fluorenyl, phenyl, naphthyl, indanyl, adamantyl, and tetrahydronaphthyl.

As used herein, the term "heterocycle" or "heterocyclic system" is intended to mean a stable 5-to 7-membered mono-cyclic or bicyclic or 7-to 10-membered bicyclic het-erocyclic ring which is saturated partially unsaturated or unsaturated (aromatic), and which consists of carbon atoms and from 1 to 4 heteroatoms independently selected from the group consist-ing of N, O and S and including any bicyclic group in which any of the above-defined heterocyclic rings is fused to a benzene ring. The nitrogen and sulfur heteroa-toms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitro-gen in the heterocycle may optionally be quaternized. It is preferred that when the total number of S and O atoms in the heterocycle exceeds 1, then these heteroatoms are not adja-cent to one another. It is preferred that the total number of S and O atoms in the heterocycle is not more than 1. As used herein, the term "aromatic heterocyclic system" or "het-eroaryl" is intended to mean a stable 5-to 7-membered monocyclic or bicyclic or 7-to 10-membered bicyclic hetero-cyclic aromatic ring that consists of carbon atoms and from 1 to 4 heterotams independently selected from N, O and S. It is preferred that the total number of S and O atoms in the aromatic heterocycle is not more than 1.

Examples of heterocycles include, but are not limited to, acridinyl, azocinyl, benzimidazolyl, benzofuranyl, ben-zothiofuranyl, benzothiophenyl, benzoxazolyl, benzthiazolyl, benztriazolyl, benztetrazolyl, benzisoxazolyl, benzisothi-azolyl, benzimidazolinyl, carbazolyl, 4aH-carbazolyl, carbonlinyl, chromanyl, chromenyl, cinnolinyl, decahydroquinolin-yl, 2H,6H-1,5,2-dithiazinyl, dihydrofuro [2,3-b]tetrahydro-furan, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoind-azolyl, isoindolinyl, isoindolyl, isoquinolinyl, isothiazo-lyl, isoxazolyl, methylenedioxyphenyl, morpholinyl, naphthayridinyl, octahydroisoquinolinyl, oxadiazolyl, 1,2,3-oxadi-azolyl, 1,2,4-oxadiazolyl, 1,2,5-oxadiazolyl, 1,3,4-oxadi-azolyl, oxazolidinyl, oxazolyl, oxazolidinyl, pyrimidinyl, phenanthridinyl, phenanthrolinyl, phenazinyl, phenothi-azinyl, phenoxathiinyl, phenoxazinyl, phthalazinyl, piperazinyl, piperidinyl, pteridinyl, purinyl, pyranyl, pyrazin-yl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquin-olinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothi-azolyl, thienooxazolyl, thienoimidazolyl, thiophenyl, triazinyl, 1,2,3-triazolyl, 1,2,4-triazolyl, 1,2,5-triazolyl, 1,3, 4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids,such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenyl-alanine, homocysteine, homoserine, ornithine, 3-monoiodo-tyrosine, 3,5-diiodotryosine, 3,5,5'-triiodothyronine, and 3,3',5,5'-tetraiodothyronine. Modified or unusual, amino acids which can be used to practice the invention include, but are not limited to, D-amino acids, hydroxylysine, 4-hydroxyproline, an N-Cbz-protected amino acid, 2,4-di-aminobutyric acid, homoargininel norleucine, N-methylamino-butyric acid, naphthylalanine, phenylglycine, β-phenylpro-line, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexane-carboxylic acid, 2-, 3-, and 4-(aminomethyl)-benzoic acid, 1-aminocyclopentanecarboxylic acid, 1-aminocyclopropanecar-boxylic acid, and 2-benzyl-5-aminopentanoic acid.

The term "peptide" as used herein means a linear com-pound that consists of two or more amino acids (as defined herein) that are linked by means of a peptide bond. A "peptide" as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomi-metic residues or other non-amino acid components. Such a compound containing both peptide and non-peptide compo-nents may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseu-dopeptide residue" means that portion of an pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The term "non-peptide" refers to a compound in comprised of preferably less than three amide bonds in the backbone core compound or preferably less than three amino acids or amino acid mimetics.

A "diagnostic kit" or "kit" is a collection of components, termed the formulation, in one or more vials that are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required equipment necessary for administering the radiopharmaceutical to the patient such as syringes and shielding, and imaging equipment.

Buffers useful in the preparation of metallopharmaceuticals and in diagnostic kits for the preparation of the radiopharmaceuticals include but are not limited to phosphate, citrate, sulfosalicylate and acetate. A more complete list can be found in the United States Pharmacopeia.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N, N',N'-ethylenediaminetetraacetic acid, pyrophosphate and methylenediphosphonate. In general, transfer ligands are comprised of oxygen or nitrogen donor atoms.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits for the preparation of the radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts in-clude, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavail-ability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Pro-drugs the present invention are prepared by modifying functional groups present in the compound in such a way that the modifications are cleaved, either in routine manipula-tion or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The coordination sphere of the radionuclide includes all the ligands or groups bound to the radionuclide. For a transition metal radionuclide, $M_r$, to be stable it typically has a coordination number (number of donor atoms) comprised of an integer greater than or equal to 4 and less than or equal to 9; that is there are 4 to 9 atoms bound to the metal and it is said to have a complete coordination sphere. The requisite coordination number for a stable radionuclide complex is determined by the identity of the radionuclide, its oxidation state, and the type of donor atoms.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid and inositol.

Solubilization aids useful in the preparation of radiopharmaceuticals and in diagnostic kits for the preparation of the radiopharmaceuticals include but are not limited to ethanol, glycerin, polyethylene glycol, propylene glycol, polyoxyethylene sorbitan monooleate, sorbitan monooleate, polysorbates, poly(oxyethylene)poly(oxypropylene)poly(oxy-ethylene) block copolymers (Pluronics) and lecithin. Preferred solubilizing aids are polyethylene glycol and Pluronics.

Bacteriostats useful in the preparation of radiopharmaceuticals and in diagnostic kits useful for the preparation of said radiopharmaceuticals include but are not limited to benzyl alcohol, benzalkonium. chloride, chlorbutanol, and methyl, propyl or butyl paraben.

The technetium and rhenium radiopharmaceuticals of the present invention can be easily prepared by admixing a salt of a radionuclide, a compound of the present invention, and a reducing agent, in an aqueous solution at temperatures from 0 to 100° C. The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99 m generators. The amount of pertechnetate used to prepare the radiopharmaceuticals of the present invention can range from 0.1 mCi to 1 Ci, or more preferably from 1 to 200 mCi.

The amount of the compounds of the present invention used to prepare the technetium and rhenium radiopharmaceuticals of the present invention can range from 0.01 μg to 10 mg, or more preferably from 0.5 μg to 200 μg. The amount used will be dictated by the amounts of the other reactants and the identity of the radiopharmaceuticals of the present invention to be prepared.

The metallopharmaceuticals of the present invention comprised of a metal of atomic number 21–31, 39–43, 44–50, 56–74, 76–80, 82–83, and 90 can be easily prepared by admixing a salt of a radionuclide and a reagent of the present invention, in an aqueous solution at temperatures from 0 to 100° C. These metals (radioisotopes, paramagnetic metals, and X-ray absorbing metals) are typically obtained as a dilute aqueous solution in a mineral acid, such as hydrochloric, nitric or sulfuric acid. The metals are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the metallopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

The bio-targeted pharmaceuticals of the present invention have the formulae, $(BM)_d-L_n-(C_h-X)$, and $(BM)_d-L_n-(C_h-X^1)_d$, wherein BM represents a peptide, polypeptide, peptidomimetic, or non-peptide that binds to a receptor or enzyme expressed or up-regulated in angiogenic tumor vasculature, d is 1–10, $L_n$ represents an optional linking group, $C_h$ represents a novel metal chelator of the present invention, d' is 1–100, X represents a radioisotope, and $X^1$ represents paramagnetic metal ion.

The pharmaceuticals of the present invention can be synthesized by several approaches. One approach involves the synthesis of the targeting peptide, polypeptide, peptidomimetic or non-peptide moiety, BM, and direct attachment of one or more moieties, BM, to one or more metal chelators, $C_h$. Another approach involves the attachment of one or more moieties, BM, to the linking group, $L_n$, which is then attached to one or more metal chelators, $C_h$. Another approach, useful in the synthesis of pharmaceuticals wherein d is 1, involves the synthesis of the moiety, BM—$L_n$, together, by incorporating group bearing $L_n$ into the synthesis of the peptide, polypeptide, peptidomimetic, or non-peptide. The resulting moiety, BM-$L_n$, is then attached to one or more metal chelators, $C_h$. Another approach involves the synthesis of a peptide, polypeptide, peptidomimetic, or non-peptide, BM, bearing a fragment of the linking group, $L_n$, one or more of which are then attached to the remainder of the linking group and then to one or more metal chelators, $C_h$.

The peptides, polypeptides, peptidomimetics and. non-peptides, BM, optionally bearing a linking group, $L_n$, or a fragment of the linking group, can be synthesized using standard synthetic methods known to those skilled in the art. Preferred methods include but are not limited to those methods described below.

Generally, peptides, polypeptides, and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield (J. Am. Chem. Soc. 1963 85, 2149–2154), the disclosure of which is hereby incorporated by reference.

The peptides, polypeptides and peptidomimetics may also be synthesized using automated synthesizing equipment. In addition to the foregoing, procedures for peptide, polypeptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, polypeptide or peptidomimetic, two peptide, polypeptide or peptidomimetic fragments, or the cyclization of a peptide, polypeptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-C, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology", Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide, polypeptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide, polypeptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free α-carboxylate and a free α-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology", Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated herein by reference.

Additional synthetic procedures that can be used by one of skill in the art to synthesize the peptides, polypeptides and peptidomimetics targeting moieties are described in co-pending applications: U.S. application Ser. No. 08/943,659, U.S. application Ser. No. 09/281,474, U.S. application Ser. No. 09/466,588, U.S. application Ser. No. 09/465,300, U.S. application Ser. No. 09/466,582, U.S. application Ser. No. 60/182,627, and U.S. application Ser. No. 60/182,712, the contents of which are herein incorporated by reference.

The attachment of linking groups, $L_n$, to the peptides, polypeptides, peptidomimetics and non-peptide, BM; chelators, $C_h$, to the peptides, polypeptides, peptidomimetics, and non-peptides, W, or to the linking groups, $L_n$; and peptides, polypeptides, peptidomimetics, and non-peptides bearing a fragment of the linking group to the remainder of the linking group, in combination forming the moiety, $(BM)_d-L_n$, and then to the moiety $C_h$; can all be performed by standard techniques. These include, but are not limited to, amidation, esterification, alkylation, and the formation of ureas or thioureas. Procedures for performing these attach-ments can be found in Brinkley, M., *Bioconjugate Chemistry* 1992, 3(1), which is incorporated herein by reference.

The linking group $L_n$ can serve several roles. First it provides a spacing group between the metal chelator, and the one or more of the peptides, polypeptides, peptidomimetics, or non-peptides, BM, so as to minimize the possibility that the moieties $C_h-X$, $C_h-X^1$, will interfere with the interaction of the recognition sequences of BM with the target receptors. The necessity of incorporating a linking group in a reagent is dependent on the identity of BM, $C_h-X$, and $C_h-X^1$. If $C_h-X$, and $C_h-X^1$, cannot be attached to BM without substantially diminishing its affinity for the receptors, then a linking group is used. A linking group also provides a means of independently attaching multiple peptides, polypeptides, peptidomimetics, and non-peptides, BM, to one group that is attached to $C_h-X$, or $C_h-X^1$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, BM, with the target receptors. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route, of elimination of the pharmaceuticals. Preferred pharmacokinetic modifiers are those that result in moderate to fast blood clearance and enhanced renal excretion.

For the diagnosis of thromboembolic disorders or atherosclerosis, BM is selected from the group including the cyclic IIb/IIIa receptor antagonist compounds described in U.S. Pat. No. 5,879,657; the RGD containing peptides described in U.S. Pat. Nos. 4,578,079 and 4,792,525, the PCT applications Wo 8905150, WO 8910135, WO 9101331, and WO 9115515 and by Ojima et. al., 204th Meeting of the Amer. Chem. Soc., 1992, Abstract 44; the peptides that are fibrinogen receptor antagonists described in European Patent Application Nos. EP 410537, EP 410539, EP 410541, EP 422937, EP 422938, EP 425212, the specific binding peptides and polypeptides described as IIb/IIIa receptor ligands, ligands for the polymerization site of fibrin, laminin derivatives, ligands for fibrinogen, or thrombin ligands in WO 93/23085 (excluding the technetium binding groups); the oligopeptides that correspond to the IIIa protein described in WO 90/00178; the hirudin-based peptides described in WO 90/03391; the IIb/IIIa receptor ligands described in WO 90/15818; the thrombus, platelet binding or atherosclerotic plaque binding peptides described in WO 92/13572 (excluding the technetium binding group) or GB 2258494 and WO 9318160; the fibrin binding peptides described in U.S. Pat. Nos. 4,427,646 and 5,270,030; the hirudin-based peptides described in U.S. Pat. No. 5,279,812; the fibrin binding proteins described in U.S. Pat. No. 5,217,705; the guanine derivatives that bind to the IIb/IIIa receptor described in U.S. Pat. No. 5,086,069; or the tyrosine derivatives described in published European Patent Application No. 478,328, and by Hartman et. al., J. Med. Chem., 35, 4640 (1992); or oxidized low density lipoprotein (LDL).

For the diagnosis of infection, inflammation or transplant rejection, BM is selected from the group including the leukocyte binding peptides described in WO 93/17719 (excluding the technetium binding group), WO 92/13572 (excluding the technetium binding group) or U.S. patent application Ser. No. U.S. Pat. No. 5,792,444; the chemotactic peptides described in Eur. Pat. Appl. EP 398143 or A. Fischman et. al., Semin. Nuc. Med., 24, 154 (1994); the leukostimulatory agents described in U.S. Pat. No. 5,277,892; or the LTB4 antagonists described in co-pending U.S. Ser. No. 08/943,659.

For the diagnosis of cancer, BM is selected from the group of somatostatin analogs described in UK Application 8927255.3 or WO 94/00489, the selectin binding peptides described in WO 94/05269, the biological-function domains described in WO 93/12819, Platelet Factor 4 or the growth factors (PDGF, VEGF, EGF, FGF, TNF, MCSF or the interleukins Il 1–8).

BM may also be a compound that binds a receptor that is expressed or upregulated in angiogenic tumor vasculature. For targeting the VEGF receptors, Flk-1/KDR, Flt-1, and neuropilin-1, the targeting moieties are comprised of peptides, polypeptides or peptidomimetics that bind with high affinity to the receptors. For example, peptides comprised of a 23 amino acid portion of the C-terminal domain of VEGF have been synthesized which competitively inhibit binding of VEGF to VEGFR (Soker, et. al., J. Biol. Chem., 272, 31582–8 (1997)). Linear peptides of 11 to 23 amino acid residues that bind to the basic FGF receptor (bFGFR) are described by Cosic et. al., Mol. and Cell. Biochem., 130, 1–9 (1994). A preferred linear peptide antagonist of the bFGFR is the 16 amino acid peptide, Met-Trp-Tyr-Arg-Pro-Asp-Leu-Asp-Glu-Arg-Lys-Gln-Gln-Lys-Arg-Glu. Gho et. al. (Cancer Research, 57, 3733–40 (1997)) describe the identification of small peptides that bind with high affinity to the angiogenin receptor on the surface of endothelial cells. A preferred peptide is Ala-Gln-Leu-Ala-Gly-Glu-Cys-Arg-Glu-Asn-Val-Cys-Met-Gly-Ile-Glu-Gly-Arg, in which the two Cys residues form an intramolecular disulfide bond. Yayon et. al. (Proc. Natl. Acad. Sci, USA, 90, 10643–7 (1993)) describe other linear peptide antagonists of FGFR, identified from a random phage-displayed peptide library. Two linear octapeptides, Ala-Pro-Ser-Gly-His-Tyr-Lys-Gly and Lys-Arg-Thr-Gly-Gln-Tyr-Lys-Leu are preferred for inhibiting binding of bFGF to it receptor.

Targeting moieties for integrins expressed in tumor vasculature include peptides, polypeptides and peptidomimetics that bind to avB3, avB5, a5B1, a4B1, a1B1, and a2B2. Pierschbacher and Rouslahti (J. Biol. Chem., 262, 17294–8 (1987)) describe peptides that bind selectively to a5B1 and avB3. U.S. Pat. No. 5,536,814 describe peptides that bind with high affinity to the integrin a5B1. Burgess and Lim (J. Med. Chem., 39, 4520–6 (1996)) disclose the synthesis three peptides that bind with high affinity to avB3: cyclo[Arg-Gly-Asp-Arg-Gly-Asp], cyclo[Arg-Gly-Asp-Arg-Gly-D-Asp] and the linear peptide Arg-Gly-Asp-Arg-Gly-Asp. U.S. Pat. Nos. 5,770,565 and 5,766,591 disclose peptides that bind with high affinity to avB3. U.S. Pat. Nos. 5,767,071 and 5,780,426, disclose cyclic peptides that have an exocyclic Arg amino acid that have high affinity for avB3. Srivatsa et. al., (Cardiovascular Res., 36, 408–28 (1997)) describe the cyclic peptide antagonist for avB3, cyclo[Ala-Arg-Gly-Asp-Mamb]. Tran et. al., (Bioorg. Med. Chem. Lett., 7, 997–1002 (1997)) disclose the cyclic peptide cyclo[Arg-Gly-Asp-Val-Gly-Ser-BTD-Ser-Gly-Val-Ala] that binds with high affinity to avB3. Arap et. al. (Science, 279, 377–80 (1998)) describe cyclic peptides that bind to avB3 and avB5, Cys-Asp-Cys-Arg-Gly-Asp-Cys-Phe-Cys, and cyclo[Cys-Asn-Gly-Asp-Cys]. Corbett et. al. (*Biorg. Med. Chem. Lett.*, 7, 1371–6 (1997)) describe a series of avB3 selective peptidomimetics. And Haubner et. al., (*Angew. Chem. Int. Ed. Engl.*, 36, 1374–89 (1997)) disclose peptides and peptidomimetic avB3 antagonists obtained from peptide libraries.

Alternative targeting moieties for tumor vasculature include compounds that interact with receptor tyrosine kinases. Receptor tyrosine kinases (TKs) are membrane proteins, which play a key role in the transduction of mitogenic signals across the cell to the nucleus (Rewcastle, G. W. et al *J. Med. Chem.* 38, 3482–3487 (1995); Thompson, A. M. et al *J. Med. Chem.*, 40, 3915–3925 (1997)). Of the many TKs that have been identified and characterized, those of the epidermal growth factor receptor (EGFR) family are particularly important, and have been implicated in a variety of ectopic cell proliferative processes. The over-expression of human EGF receptor is greatly amplified in several human tumors (Fry, D. W. *Exp. Opin. Invest. Drugs*, 3, 577–595 (1994); Jardines, L. et al *Pathobiology*, 61, 268–282 (1993)), accompanied by an overphosphorylation of their protein targets. This increased phosphorylation of substrate tyrosine residues by oncogenic TK proteins is an essential step in the neoplastic transformation. Consequently, there has been great interest in developing inhibitors of TKs (TKIs) as anticancer drugs (Burke, T. R. Jr. *Drugs Future*, 17, 119–131 (1997); Chang, C. J. and Geahlen, R. *J. Nat. Prod.*, 55, 1529–1560 (1992)). The over-expression of EGF receptors in tumor cells also provides the foundation for the development of diagnostic and therapeutic radio-pharmaceuticals by attaching a chelator and a radionuclide onto the TK receptor ligand (tyrosine kinase inhibitor).

BM may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

SYNTHESIS OF NEW MACROCYCLES

Macrocyclic Chelants Based on Kojic Acid. It is known that kojic acid undergoes Mannich reactions with primary or secondary amines in the presence of excess paraformaldehyde (Molenda, et al. *J. Inorg. Biochem.*, 55, 131 (1994); Patel, et al. *Tetrahedron*, 52, 1835 (1996)). The aminomethylation occurs at the ortho position to the enolic hydroxyl group at room temperature. The hydroxymethyl group at $C_6$ (the paraposition of the enolic hydroxyl group) is relatively unreactive towards amines. In the present invention, however, it was found that kojic acid reacted with ethylenediamine-N,N'-diacetic acid (EDDA) in the presence of formaldehyde to form a novel macrocyclic chelant, $(EDDA-KA)_2$. The reaction was carried out in 90–95% ethanol under reflux for 48 h. This Mannich cyclization reaction should also be applied to other N,N'-disubstituted ethylenediamines or N,N'-disubstituted propylenediamines (Scheme I). The presence of the two carboxylic groups may play a significant role in the cyclization, and in the relative orientation of the two pyrone groups in $(EDDA-KA)_2$ due to the strong hydrogen bonding between the amine (N—H) and the pyrone-O.

Scheme I
Synthesis of Mannich Bases from Kojic acid.

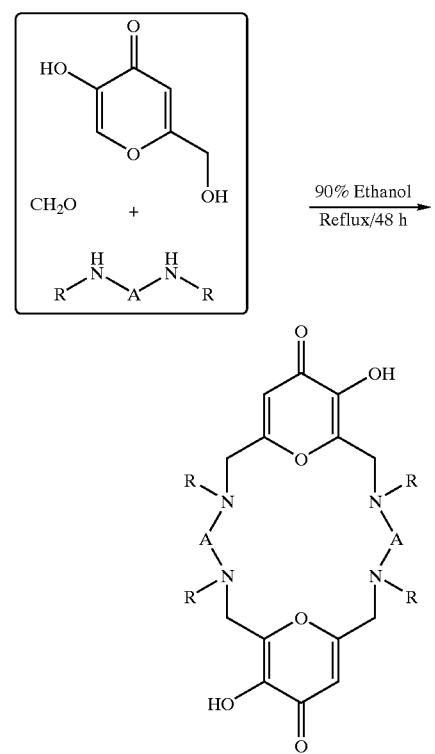

$A = A^1$ and $A^2$; $R = R^1, R^2, R^3,$ and $R^4$

Scheme II
Reaction Mechanism for (EDDA-KA)$_2$.

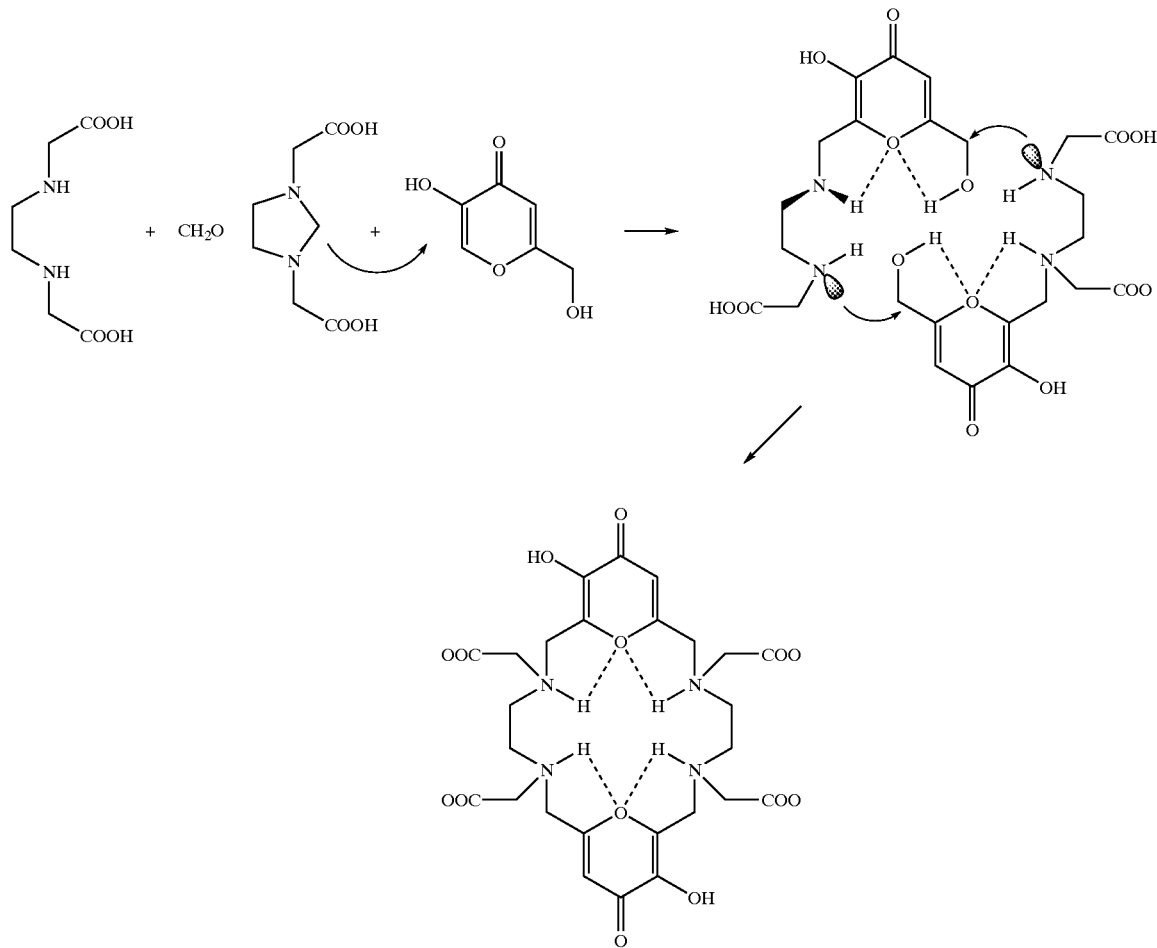

The Mannich reaction can proceed through two pathways (Tramontini, M and Angiolini, L. *Tetrahedron*, 46, 1791 (1990)) and is usually a result of a complex series of equilibria, related to the nature of the reactants and reaction conditions, which deterimine the preferred mechanism. For EDDA, it reacts with paraformaldehyde first to form a substituted five-membered imidazolidine intermediate (Scheme II), which undergoes rapid electrophilic reaction at the ortho position of the enolic hydroxyl group to give the EDDA-KA adduct. Due to the N-substitution, and amine-N. becomes more basic and the proton of the carboxylic group will be shifted to amine-N to form Zwitterion. The N-H group forms a strong hydrogen bonding with pyrone-O atom, which makes the 6-hydroxylmethyl group more reactive towards the remaining amine-N (Scheme II) of another EDDA-KA intermediate.

Scheme III
Syntesis of Mannich Bases from N-Substituted 3-Hydroxyl-4[1H]-Pyridinones.

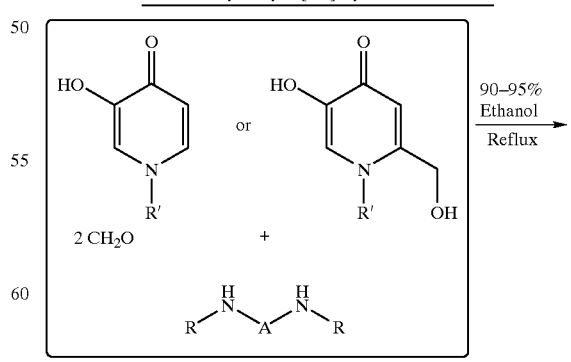

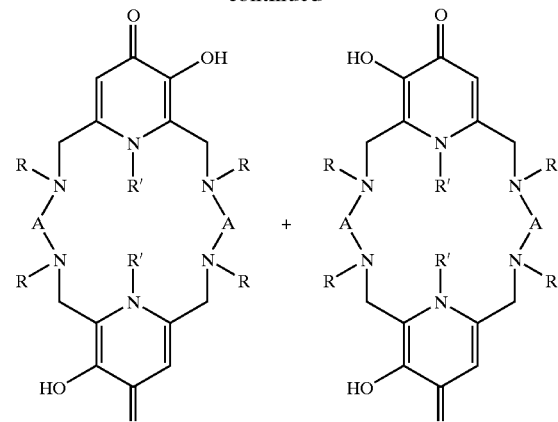

A = A¹ and A²; R = R¹, R², R³, and R⁴

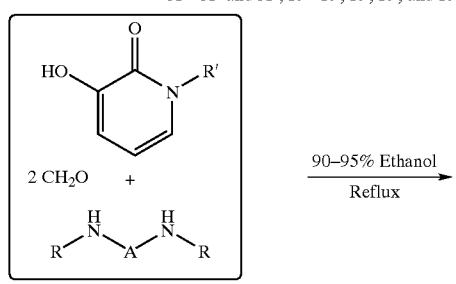

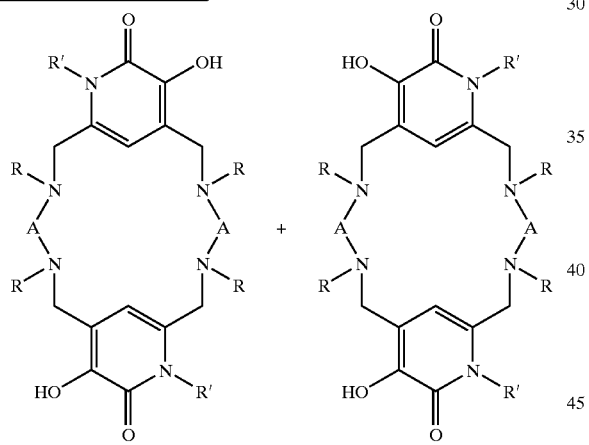

A = A¹ and A²; R = R¹, R², R³, and R⁴

Macrocyclic Chelants Based on N-Substituted 3-Hydroxyl-4 [1H]-Pyridinones. Like kojic acid, N-substituted 3-hydroxyl-4 [1H]-pyridinones also undergo Mannich reactions secondary amines in the presence of excess paraformaldehyde (Patel, et al. *Tetrahedron*, 52, 1835 (1996); Nakamura,A. and Kamiya, S. *Chem. Pharm. Bull.*, 16, 1466 (1968)). In general, the aminomethylation occurs at the ortho position to the enolic hydroxyl group at room temperature while the aminomethylation at the para-position to the enolic hydroxyl group) requires higher temeprature under reflux conditions. Scheme III shows a general procedure for the synthesis of macrocyclic Mannich bases from N-substituted 3-hydroxyl-4 [1H] -pyridinones. Both N-substituted 3-hydroxyl-4 [1H]-pyridinones and N-substituted 3-hydroxyl-4 [1H]-6-hydroxymethylpyridinones can be used as the starting materials.

EXPERIMENTAL

Instruments. The $^1$H NMR spectra data were obtained on a 600 MHz Bruker spectrometer. Electrospray MS analyses were performed using a VG Quattro mass spectrometer. LC-MS spectra were collected using a HP1100 LC/MSD system with API-electrospray interface. Ethylenediamine-N, N'-diaacetic acid (EDDA), kojic acid, and paraformaldehyde were purchased from Aldrich, and were used as received.

EXAMPLE I

Synthesis of (EDDA-KA)$_2$

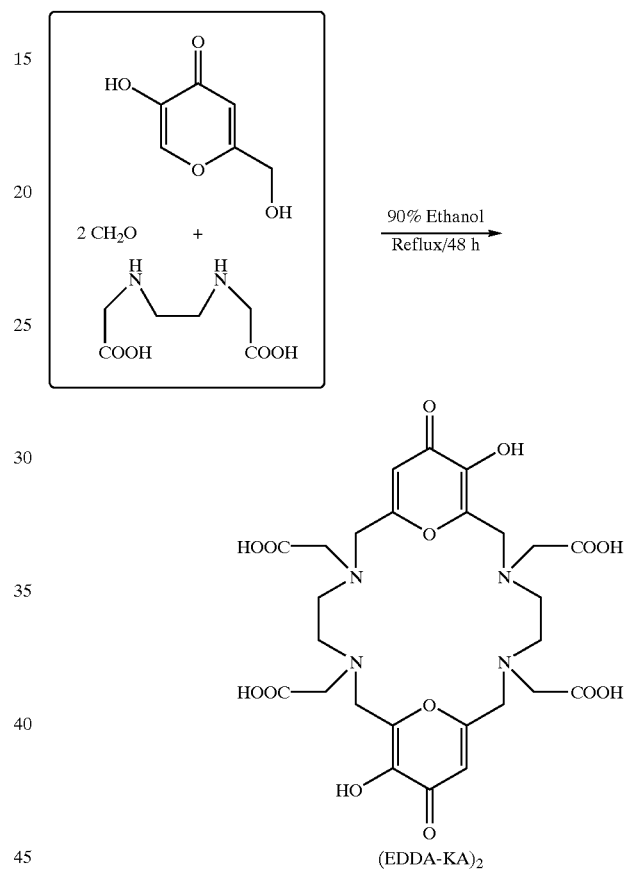

(EDDA-KA)$_2$

To a suspension of EDDA (1.75 g, 10 mmole) in 90% ethanol (180 mL) was added paraformaldehyde (0.8 g, 26.7 mmole), and kojic acid (3.0 g, 21 mmole). The reaction mixture was heated to reflux for 48 hours. The mixture was cooled to root temperature, and the resulting solid was collected by filtration, washed with ethanol, and dried under vacuum overnight. The yield was 2.95 g (94%). The crude product was dissolved in minimum amount of sodium hydroxide solution (5 N). The mixture was filtered, and to the filtrate was added dropwise the concentrated HCl solution until a large amount of precipitate formed. The solid was collected by filtration, washed with ethanol, and dried under vacuum overnight. Anal. calcd (found) for $C_{26}H_{32}N_4O_{14} \cdot 1.5H_2O$: C, 47.93 (47.93); H, 5.31 (5.41); N, 8.56 (8.60). Electrospray MS: M/z=625.1 for $[C_{26}H_{33}N_4O_{14}]^+$, 313 for $[C_{26}H_{34}N_4O_{14}]^{2+}$. $^1$H NMR (600 MHz, in D$_2$O, chemical shift in ppm relative to TMS): 2.85 (t, 4H, CH$_2$); 3.40 (s, 4H, CH$_2$); 3.48 (t, 4H, CH$_2$); 3.5 (s, 4H, CH$_2$), 3.70 (s, 4H, CH$_2$); 4.50 (s, 4H, CH$_2$); and 6.45 (s, 2H, pyridinone).

EXAMPLE II

Synthesis of $^{111}$In Complex of (EDDA-KA)$_2$

To a 5 mL vial containing 0.5 mL of the (EDDA-KA)$_2$ solution (4 mg/mL in 0.5 M NH$_4$OAc, pH=8.0) was added 20 μL of $^{111}$InCl$_3$ solution (~0.2 mCi) in 0.05 N HCl. The reaction mixture was heated at 80° C. for 10 min. After cooling to room temperature, the resulting solution was analyzed by an ITLC method using Gelman Sciences silicon gel paper strip, and a 50:50 mixture of saline and acetone as mobile phase. Using this method, $^{111}$InCl$_3$ and [$^{111}$In]acetate remain at the origin while the radiolabeled (EDDA-KA)$_2$ migrates to the solvent front. The yield was 96.8%.

EXAMPLE III

Synthesis of $^{90}$Y Complex of (EDDA-KA)$_2$

To a 5 mL vial containing 0.5 mL of the (EDDA-KA)$_2$ solution (4 mg/mL in 0.5 M NH$_4$OAc, pH=8.0) was added 3 μL of $^{90}$YCl$_3$ solution (~3 mCi) in 0.05 N HCl. The reaction mixture was heated at 80° C. for 10 min. After cooling to room temperature, the resulting solution was analyzed by an ITLC method using Gelman Sciences silicon gel paper strip, and a 50:50 mixture of saline and acetone as mobile phase. Using this method, $^{90}$Ycl$_3$ and [$^{90}$Y]acetate remain at the origin while the radiolabeled (EDDA-KA)$_2$ migrates to the solvent front. The yield was 99.8%.

EXAMPLE IV

Synthesis of $^{177}$Lu Complex of (EDDA-KA)$_2$

To a 5 mL vial containing 0.5 mL of the (EDDA-KA)$_2$ solution (4 mg/mL in 0.5 M NH$_4$OAc, pH=8.0) was added 2 μL of $^{177}$LuCl$_3$ solution (2 mCi) in 0.05 N HCl. The reaction mixture was heated at 80° C. for 10 min. After cooling to room temperature, the resulting solution was analyzed by an ITLC method using Gelman Sciences silicon gel paper strip, and a 50:50 mixture of saline and acetone as mobile phase. Using this method, $^{177}$LuCl$_3$ and [$^{177}$Lu]acetate remain at the origin while the radiolabeled (EDDA-KA)$_2$ migrates to the solvent front. The yield was 87.8%.

UTILITY

The diagnostic radiopharmaceuticals are administered by intravenous injection, usually in saline solution, at a dose of 1 to 100 mCi per 70 kg body, weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. No. 5,155,215; U.S. Pat. No. 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The pharmaceuticals of the present invention are useful for imaging hypoxia, apoptosis, cardiac ischemia, thrombosis, infection, inflammation, cancer, restenosis, atherosclerosis, diabetic retinopathy, macular degeneration, wound healing, and reperfusion injury, in a patient. The imaging radiopharmaceuticals of the present invention comprised of a gamma ray or positron emitting isotope. The radiopharmaceuticals of the present invention comprised of a beta, alpha or Auger electron emitting isotope are useful for treatment of pathological processes including cancer, rstenosis, diabetic retinopathy, and macular degeneration, by delivering a cytotoxic dose of radiation to the locus of expression of the receptor or enzyme with which the BM interacts (targets). The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of hypoxia, apoptosis, cardiac ischemia, thrombosis, infection, inflammation, cancer, restenosis, atherosclerosis, diabetic retinopathy, macular degeneration, wound healing, and reperfusion injury.

The compounds of the present invention comprised of one or more heavy atoms with atomic number of 20, or greater are useful as X-ray contrast agents for X-ray imaging of hypoxia, apoptosis, cardiac ischemia, thrombosis, infection, inflammation, cancer, restenosis, atherosclerosis, diabetic retinopathy, macular degeneration, wound healing, and reperfusion injury.

Biochemical assays and in vivo models for testing the pharmaceuticals of the present invention are described in U.S. Pat. No. 5,879,657, PCT Application WO 98/15295, and PCT Application WO 99/51628. The assays and models described are incorporated herein by reference.

Obviously, numerous modifications and variations of the present invention are possible in light of the above teachings. It is therefore to be understood that within the scope of the appended claims, the invention may be practiced otherwise that as specifically described herein.

What is claimed is:

1. A macrocyclic chelant having the formula:

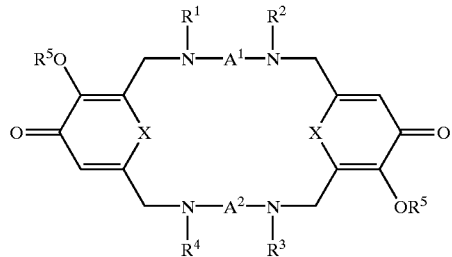

and pharmaceutically acceptable salts thereof,
wherein A$^1$ and A$^2$ are independently —(CH$_2$)$_n$—, wherein n is 2 or 3;
X is selected from the group consisting of O, NH and N(OH);
R$^1$, R$^2$, R$^3$, R$^4$ and R$^5$ are independently selected from the group consisting of H, C$_1$–C$_{10}$ alkyl substituted with 1–5 R$^6$, C$_1$–C$_{10}$ fluoroalkyl substituted with 1–5 R$^6$, $C_2$–$C_{10}$ alkenyl substituted with 1–5 $R^6$, $C_2$–$C_{10}$ fluoroalkenyl substituted with 1–5 $R^6$, and aryl substituted with 1–5 $R^6$ and fluoroaryl substituted with 1–5 $R^6$;

$R^6$ is selected from the group consisting of H, C(=O)$R^7$, C(=O)O$R^8$, C(=O)N$R^7R^8$, PO(O$R^7$)(O$R^8$) and S(O)$_2$O$R^7$;

$R^7$ and $R^8$ are independently selected from the group consisting of H, $C_1$–$C_{10}$ alkyl substituted with 0–5 $R^9$, $C_3$–$C_{10}$ cycloalkyl substituted with 0–5 $R^9$, $C_1$–$C_{10}$ fluoroalkyl substituted with 0–5 $R^9$, $C_2$–$C_{10}$ alkenyl substituted with 0–5 $R^9$, $C_2$–$C_{10}$ fluoroalkenyl substituted with 0–5 $R^9$, aryl substituted with 0–5 $R^9$ and fluoroaryl substituted with 0–3 $R^9$, or $R^7$ and $R^8$ may be taken together to form $C_3$–$C_{10}$ cycloalkyl or $C_3$–$C_{10}$ cycloalkenyl optionally interrupted with O, S, NH, S(O), S(O)$_2$, P(O)(O$R^{10}$)O, P(O)(NH$R^{10}$)O, C(O)NH, NHC(O), NHC(O)NH, NHC(S)NH, or to form aryl substituted with 0–5 $R^{10}$ or fluoroaryl substituted with 0–5 $R^{10}$; said $C_1$–$C_{10}$ alkyl or $C_2$–$C_{10}$ alkenyl optionally interrupted with O, S, N$R^{10}$ S(O), S(O)$_2$, P(O)(O$R^{10}$), P(O)(O$R^{10}$)O, P(O)(NH$R^{10}$), P(O)(NH$R^{10}$)O, C(O)NH, NHC(O), NHC(O)NH or NHC(S)NH;

$R^9$ is selected from the group consisting of H, OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$; and $R^{10}$ is selected from the group consisting of H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl and fluorophenyl.

2. A chelant according to claim 1, wherein:

$A^1$ and $A^2$ are —(CH$_2$)$_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of C(=O)$R^7$, C(=O)O$R^8$, C(=O)N$R^7R^8$, PO(O$R^7$)(O$R^8$) and S(O)$_2$O$R^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$.

3. A chelant according to claim 2, wherein:

X is O or NH;

$R^1$, $R^2$, $R^3$, $R^4$ and $R^5$ are independently selected from the group consisting of H, CH$_2$COOH, CH$_2$C(=O)N$R^7R^8$, CH$_2$PO(O$R^7$)(O$R^8$) and CH$_2$S(O)$_2$OH; and $R^7$ and $R^8$ are independently selected from the group consisting of $C_1$–$C_3$ alkyl substituted with 0–2$R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

4. A chelant according to claim 3, wherein $R^1$, $R^2$, $R^3$, $R^4$ and $R^5$ are independently selected from the group consisting of H, CH$_2$COOH, CH$_2$C(=O)NH$_2$, CH$_2$PO(OH)$_2$ and CH$_2$S(O)$_2$OH.

5. A chelant according to claim 4, having the structure:

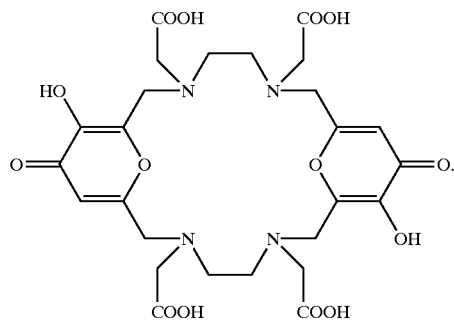

6. A radiopharmaceutical compound comprising a chelant according to claim 1, chelated with a radionuclide selected from the group consisting of $^{52m}$Mn, $^{52}$Fe, $^{55}$Co, $^{60}$Cu, $^{62}$Cu, $^{64}$Cu, $^{67}$Cu, $^{67}$Ga, $^{68}$Ga, $^{90}$Y, $^{94m}$Tc, $^{99m}$Tc, $^{105}$Rh, $^{109}$Pd, $^{111}$In, $^{117m}$Sn, $^{149}$Pr, $^{153}$Sm, $^{159}$Gd, $^{166}$Ho, $^{169}$Yb, $^{177}$Lu, $^{186}$Re, $^{188}$Re, $^{203}$Pb, $^{211}$Pb, and $^{212}$Bi.

7. A radiopharmaceutical compound according to claim 6, wherein:

$A^1$ and $A^2$ are —(CH$_2$)$_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of C(=O)$R^7$, C(=O)O$R^8$, C(=O)N$R^7R^8$, PO(O$R^7$)(O$R^8$) and S(O)$_2$O$R^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$.

8. A radiopharmaceutical compound according to claim 7, wherein:

X is O or NH;

$R^1$, $R^2$, $R^3$, $R^4$ and $R^5$ are independently selected from the group consisting of H, CH$_2$COOH, CH$_2$C(=O)N$R^7R^8$, CH$_2$PO(O$R^7$)(O$R^8$) and CH$_2$S(O)$_2$OH; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

9. A radiopharmaceutical compound according to claim 8, wherein $R^1$, $R^2$, $R^3$, $R^4$ and $R^5$ are independently selected from the group consisting of H, CH$_2$COOH, CH$_2$C(=O)NH$_2$, CH$_2$PO(OH)$_2$ and CH$_2$S(O)$_2$OH.

10. A radiopharmaceutical compound according to claim 4, wherein said chelant has the structure:

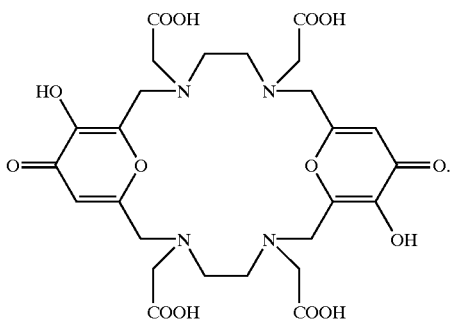
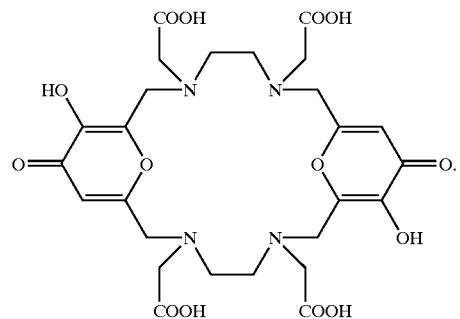

11. An MRI contrast agent comprising a chelant according to claim 1, chelated with a paramagnetic metal ion of atomic number 21–29, 42–44 or 58–70.

12. An MRI contrast agent according to claim 11, wherein:

$A^1$ and $A^2$ are —$(CH_2)_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of C(=O)$R^7$, C(=O)O$R^8$, C(=O)N$R^7R^8$, PO(O$R^7$)(O$R^8$) and S(O)$_2$O$R^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$.

13. An MRI contrast agent according to claim 12, wherein:

X is O or NH;

$R^1$, $R^2$, $R^3$, $R^4$ and $R^5$ are independently selected from the group consisting of H, CH$_2$COOH, CH$_2$C(=O)N$R^7R^8$, CH$_2$PO(O$R^7$)(O$R^8$) and CH$_2$S(O)$_2$OH; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

14. An MRI contrast agent according to claim 13, wherein $R^1$, $R^2$, $R^3$, $R^4$ and $R^5$ are independently selected from the group consisting of H, CH$_2$COOH, CH$_2$C(=O)NH$_2$, CH$_2$PO(OH)$_2$ and CH$_2$S(O)$_2$OH.

15. An MRI contrast agent according to claim 14, wherein said chelant has the structure:

16. An X-ray or CT contrast agent comprising a chelant according to claim 1, chelated with a heavy metal ion of atomic number 21–31, 39–50, 56–80, 82, 83 or 90.

17. An X-ray or CT contrast agent according to claim 16, wherein:

$A^1$ and $A^2$ are —$(CH_2)_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of C(=O)$R^7$, C(=O)O$R^8$, C(=O)N$R^7R^8$, PO(O$R^7$)(O$R^8$) and S(O)$_2$O$R^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, NH$R^{10}$, C(=O)$R^{10}$, OC(=O)$R^{10}$, OC(=O)O$R^{10}$, C(=O)O$R^{10}$, C(=O)N$R^{10}_2$, PO$_3R^{10}_2$, S$R^{10}$, SO$R^{10}$, SO$_2R^{10}$, NHC(=O)$R^{10}$, NHC(=O)NH$R^{10}$, CH$_2$O$R^{10}$ and NHC(=S)NH$R^{10}$.

18. An X-ray or CT contrast agent according to claim 17, wherein:

X is O or NH;

$R^1$, $R^2$, $R^3$, $R^4$ and $R^5$ are independently selected from the group consisting of H, CH$_2$COOH, CH$_2$C(=O)N$R^7R^8$, CH$_2$PO(O$R^7$)(O$R^8$) and CH$_2$S(O)$_2$OH; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

19. An X-ray or CT contrast agent according to claim 18, wherein $R^1$, $R^2$, $R^3$, $R^4$ and $R^5$ are independently selected from the group consisting of H, CH$_2$COOH, CH$_2$C(=O)NH$_2$, CH$_2$PO(OH)$_2$ and CH$_2$S(O)$_2$OH.

20. An X-ray or CT contrast agent according to claim 19, wherein said chelant has the structure:

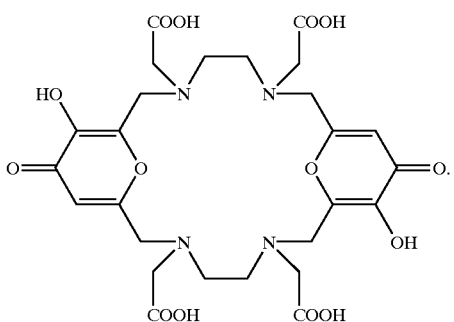

21. A conjugate of the formula:

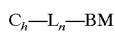

and pharmaceutically acceptable salts thereof, wherein:
- $C_h$ is a chelant according to claim 1, wherein one of $R^1$ to $R^{10}$ is optionally a bond to $L_n$;
- $L_n$ is a linking group of formula:

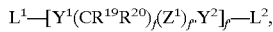

wherein $L^1$ is $-[(CH_2)_gZ^1]_{g'}-(CR^{19}R^{20})_{g''}-$;
$L^2$ is $-(CR^{19}R^{20})_{g''}-[Z^1(CH_2)_g]_{g'}-$;
g is independently 0–10;
g' is independently 0–1;
g" is independently 0–10;
f is independently 0–10;
f' is independently 0–10;
f" is independently 0–1;
$Y_1$ and $Y_2$, at each occurrence, are independently selected from the group consisting of a bond, O, $NR^{20}$, C=O, C(=O)O, OC(=O)O, C(=O)NH—, C=$NR^{20}$, S, S(O), S(O)$_2$, NHC(=O), (NH)$_2$C(=O) and (NH)$_2$C=S;
$R^{19}$ and $R^{20}$ are independently selected at each occurrence from the group consisting of H, $C_1$–$C_{10}$ alkyl substituted with 0–5 $R^{21}$, and alkaryl wherein the aryl is substituted with 0–5 $R^{21}$;
$R^{21}$ is independently selected at each occurrence from the group consisting of $NHR^{22}$, C(=O)$R^{22}$, OC(=O)$R^{22}$, OC(=O)O$R^{22}$, C(=O)O$R^{22}$, C(=O)$NR_2^{22}$, —CN, $SR^{22}$, S(O)$R^{22}$, S(O)$_2R^{22}$, NHC(=O)$R^{22}$, NHC(=O)$NHR^{22}$, NHC(=S)$NHR^{22}$ and a bond to BM;
$R^{22}$ is independently selected at each occurrence from the group consisting of H, $C_1$–$C_6$ alkyl, benzyl, phenyl, and a bond to BM; and
BM is a biologically active molecule selected from the group consisting of IIb/IIIa receptor ligands, fibrin binding peptides, leukocyte binding peptides, chemotactic peptides, LTB$_4$ receptor antagonists, somatostatin analogs, selectin binding peptides, vitronectin receptor antagonists, tyrosine kinase inhibitors, matrix metalloproteinase inhibitors, oligonucleotides, fatty acids, nitroimidazoles and carbohydrates.

22. A conjugate according to claim 21, wherein:
$A^1$ and $A^2$ are —(CH$_2$)$_2$—;
$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of C(=O)$R^7$, C(=O) O$R^8$, C(=O)$NR^7R^8$, PO(O$R^7$)(O$R^8$) and S(O)$_2$O$R^7$;
$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and
$R^9$ is selected from the group consisting of OH, $NHR^{10}$, C(=O)$R^{10}$, OC(=O)$R^{10}$, OC(=O)O$R^{10}$, C(=O)O$R^{10}$, (=O)$NR^{10}_2$, PO$_3R^{10}_2$, $SR^{10}$, SO$R^{10}$, SO$_2R^{10}$, NHC(=O)$R^{10}$, NHC(=O)$NHR^{10}$, CH$_2$O$R^{10}$ and NHC(=S) $NHR^{10}$.

23. A conjugate according to claim 22, wherein:
X is O or NH;
$R^1$, $R^2$, $R^3$, $R^4$ and $R^5$ are independently selected from the group consisting of H, CH$_2$COOH, CH$_2$C(=O)$NR^7R^8$, CH$_2$PO(O$R^7$)(O$R^8$) and CH$_2$S(O)$_2$OH; and
$R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

24. A conjugate according to claim 23, wherein $R^1$, $R^2$, $R^3$, $R^4$ and $R^5$ are independently selected from the group consisting of H, CH$_2$COOH, CH$_2$C(=O)NH$_2$, CH$_2$PO (OH)$_2$ and CH$_2$S(O)$_2$OH, provided that one of one of $R^1$ to $R^5$ is a bond to $L_n$.

25. A conjugate according to claim 24, wherein said chelant has the structure:

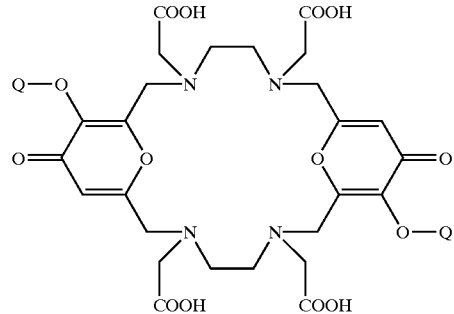

wherein Q is a bond to $L_n$.

26. A radiopharmaceutical compound comprising a conjugate according to claim 21, chelated with a radionuclide selected from the group consisting of $^{52m}$Mn, $^{52}$Fe, $^{55}$Co, $^{60}$Cu, $^{62}$Cu, $^{64}$Cu, $^{67}$Cu, $^{67}$Ga, $^{68}$Ga, $^{90}$Y, $^{94m}$Tc, $^{99m}$Tc, $^{105}$Rh, $^{109}$Pd, $^{111}$In, $^{117m}$Sn, $^{149}$Pr, $^{153}$Sm, $^{159}$Gd, $^{166}$Ho, $^{169}$Yb, $^{177}$Lu, $^{186}$Re, $^{188}$Re, $^{203}$Pb, $^{211}$Pb, and $^{212}$Bi.

27. A radiopharmaceutical compound according to claim 26, wherein:
$A^1$ and $A^2$ are —(CH$_2$)$_2$—;
$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;
$R^6$ is independently selected at each occurrence from the group consisting of C(=O)$R^7$, C(=O)O$R^8$, C(=O)$NR^7R^8$, PO(O$R^7$)(O$R^8$) and S(O)$_2$O$R^7$;
$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, $NHR^{10}$, $C(=O)R^{10}$, $OC(=O)$ $R^{10}$, $OC(=O)OR^{10}$, $C(=O)OR^{10}$, $C(=O)NR^{10}{}_2$, $PO_3R^{10}{}_2$, $SR^{10}$, $SOR^{10}$, $SO_2R^{10}$, $NHC(=O)R^{10}$, $NHC(=O)NHR^{10}$, $CH_2OR^{10}$ and $NHC(=S)NHR^{10}$.

28. A radiopharmaceutical compound according to claim 27, wherein:

X is O or NH;

$R^1$, $R^2$, $R^3$, $R^4$ and $R^5$ are independently selected from the group consisting of H, $CH_2COOH$, $CH_2C(=O)NR^7R^8$, $CH_2PO(OR^7)(OR^8)$ and $CH_2S(O)_2OH$; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

29. A radiopharmaceutical compound according to claim 28, wherein $R^1$, $R^2$, $R^3$, $R^4$ and $R^5$ are independently selected from the group consisting of H, $CH_2COOH$, $CH_2C(=O)NH_2$, $CH_2PO(OH)_2$ and $CH_2S(O)_2$ OH.

30. A radiopharmaceutical compound according to claim 29, wherein said chelant of said conjugate has the structure:

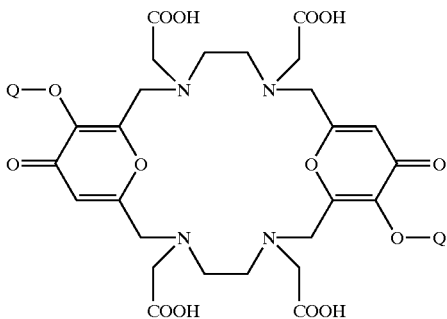

wherein Q is a bond to $L_n$.

31. An MRI contrast agent comprising a conjugate according to claim 21, chelated with a paramagnetic metal ion of atomic number 21–29, 42–44 or 58–70.

32. An MRI contrast agent according to claim 31, wherein:

$A^1$ and $A^2$ are —$(CH_2)_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of $C(=O)R^7$, $C(=O)OR^8$, $C(=O)NR^7R^8$, $PO(OR^7)(OR^8)$ and $S(O)_2OR^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, $NHR^{10}$, $C(=O)R^{10}$, $OC(=O)R^{10}$, $OC(=O)OR^{10}$, $C(=O)OR^{10}$, $C(=O)NR^{10}{}_2$, $PO_3R^{10}{}_2$, $SR^{10}$, $SOR^{10}$, $SO_2R^{10}$, $NHC(=O)R^{10}$, $NHC(=O)NHR^{10}$, $CH_2OR^{10}$ and $NHC(=S)NHR^{10}$.

33. An MRI contrast agent according to claim 32, wherein:

X is O or NH;

$R^1$, $R^2$, $R^3$, $R^4$ and $R^5$ are independently selected from the group consisting of H, $CH_2COOH$, $CH_2C(=O)NR^7R^8$, $CH_2PO(OR^7)(OR^8)$ and $CH_2S(O)_2OH$; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

34. An MRI contrast agent according to claim 33, wherein $R^1$, $R^2$, $R^3$, $R^4$ and $R^5$ are independently selected from the group consisting of H, $CH_2COOH$, $CH_2C(=O)NH_2$, $CH_2PO(OH)_2$ and $CH_2S(O)_2OH$.

35. An MRI contrast agent according to claim 34, wherein said chelant of said conjugate has the structure:

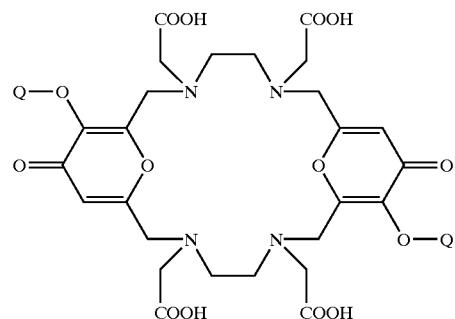

wherein Q is a bond to $L_n$.

36. An X-ray or CT contrast agent comprising a conjugate according to claim 21, chelated with a heavy metal ion of atomic number 21–31, 39–50, 56–80, 82, 83 or 90.

37. An X-ray or CT contrast agent according to claim 36, wherein:

$A^1$ and $A^2$ are —$(CH_2)_2$—;

$R^1$, $R^2$, $R^3$, $R^4$ and $R^5$ are independently selected from the group consisting of H, $C_1$–$C_3$ alkyl substituted with 1–2 $R^6$, $C_1$–$C_3$ fluoroalkyl substituted with 1–2 $R^6$, $C_2$–$C_3$ fluoroalkenyl substituted with 1–2 $R^6$, aryl substituted with 1–2 $R^6$ and fluoroaryl substituted with 1–2 $R^6$;

$R^6$ is independently selected at each occurrence from the group consisting of $C(=O)R^7$, $C(=O)OR^8$, $C(=O)NR^7R^8$, $PO(OR^7)(OR^8)$ and $S(O)_2OR^7$;

$R^7$ and $R^8$ are independently selected from the group consisting of H, $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$; and $R^9$ is selected from the group consisting of OH, $NHR^{10}$, $C(=O)R^{10}$, $OC(=O)R^{10}$, $OC(=O)OR^{10}$, $C(=O)OR^{10}$, $C(=O)NR^{10}{}_2$, $PO_3R^{10}{}_2$, $SR^{10}$, $SOR^{10}$, $SO_2R^{10}$, $NHC(=O)R^{10}$, $NHC(=O)NHR^{10}$, $CH_2OR^{10}$ and $NHC(=S)NHR^{10}$.

38. An X-ray or CT contrast agent according to claim 37, wherein:

X is O or NH;

$R^1$, $R^2$, $R^3$, $R^4$ and $R^5$ are independently selected from the group consisting of H, $CH_2COOH$, $CH_2C(=O)NR^7R^8$, $CH_2PO(OR^7)(OR^8)$ and $CH_2S(O)_2OH$; and $R^7$ and $R^8$ are independently selected from the group consisting of $C_1$–$C_3$ alkyl substituted with 0–2 $R^9$, $C_1$–$C_3$ fluoroalkyl substituted with 0–2 $R^9$, $C_2$–$C_3$ fluoroalkenyl substituted with 0–2 $R^9$, aryl substituted with 0–2 $R^9$ and fluoroaryl substituted with 0–2 $R^9$.

39. An X-ray or CT contrast agent according to claim 38, wherein $R^1$, $R^2$, $R^3$, $R^4$ and $R^5$ are independently selected from the group consisting of H, $CH_2COOH$, $CH_2C(=O)NH_2$, $CH_2PO(OH)_2$ and $CH_2S(O)_2OH$.

40. An X-ray or CT contrast agent according to claim 39, wherein said chelant of said conjugate has the structure:

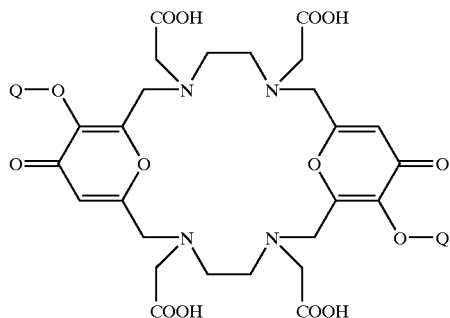

wherein Q is a bond to $L_n$.

41. A pharmaceutical composition for treating pathological processes involving angiogenic neovasculature in a patient in need thereof comprising a therapeutically effective amount of the radiopharmaceutical compound of claim 6 or the conjugate of claim 26, wherein the radionuclide is selected from the group consisting of $^{64}Cu$, $^{67}Cu$, $^{90}Y$, $^{105}Rh$, $^{109}Pd$, $^{111}In$, $^{117m}Sn$, $^{149}Pr$, $^{153}Sm$, $^{159}Gd$, $^{166}Ho$, $^{169}Yb$, $^{177}Lu$, $^{186}Re$, $^{188}Re$, $^{203Pb}$, $^{211}Pb$, and $^{212}Bi$, and a pharmaceutically acceptable carrier.

42. The composition of claim 41, comprising said radiopharmaceutical conjugate, wherein BM is selected from the group consisting of somatostatin analogs, vitronectin receptor antagonists, tyrosine kinase inhibitors, and matrix metalloproteinase inhibitors.

43. A method for treating pathological processes involving angiogenic neovasculature in a patient in need thereof comprising administering to said patient a therapeutically effective amount of the pharmaceutical composition of claim 41.

* * * * *